United States Patent [19]

Skjak-Braek et al.

[11] Patent Number: 5,459,054

[45] Date of Patent: Oct. 17, 1995

[54] CELLS ENCAPSULATED IN ALGINATE CONTAINING A HIGH CONTENT OF A- L-GULURONIC ACID

[75] Inventors: Gudmund Skjak-Braek; Olay Smidsrid; Terje Espevik; Marit Otterlei, all of Trondheim, Norway; Patrick Soon-Shiong, Los Angeles, Calif.

[73] Assignee: Neocrin Company, Irvine, Calif.

[21] Appl. No.: 85,475

[22] Filed: Jul. 2, 1993

Related U.S. Application Data

[63] Continuation of Ser. No. 619,313, Nov. 27, 1990, abandoned, which is a continuation-in-part of Ser. No. 446,462, Dec. 5, 1989, abandoned.

[51] Int. Cl.[6] .......................... C12N 11/10; C12N 11/04; C12N 5/00; A61K 37/00
[52] U.S. Cl. .................... 435/178; 435/182; 435/240.22; 424/93.7
[58] Field of Search ..................... 435/178, 179, 435/182, 240.22; 436/529; 530/813; 424/422, 424, 425, 488, 461, 93.7; 514/54, 779

[56] References Cited

U.S. PATENT DOCUMENTS

| | | | |
|---|---|---|---|
| 4,352,883 | 10/1982 | Lim | 435/178 |
| 4,407,957 | 10/1983 | Lim | 435/178 |
| 4,663,286 | 5/1987 | Tsang et al. | 435/178 |
| 4,950,600 | 8/1990 | Tanaka et al. | 435/178 |

*Primary Examiner*—David M. Naff
*Attorney, Agent, or Firm*—Lyon & Lyon

[57] ABSTRACT

Cells such as mammalian or genetically modified cells are encapsulated in high-G alginate that provokes reduced immune response during transplantation or implantation. The alginate contains greater than 50% α-L-guluronic acid and a minimal amount of mannuronic acid. The amount of α-L-guluronic acid is preferably at least 65% and more preferably at least 85%. Encapsulation is carried out by suspending cells in a solution of the high-G alginate, forming drops of the solution and contacting the drops with calcium ions to gel the alginate and form microcapsules containing the cells. The microcapsules may contain multiple layers with the high-G alginate preferably forming the outermost layer.

2 Claims, 6 Drawing Sheets

CELLS ENCAPSULATED IN ALGINATE CONTAINING A HIGH CONTENT OF A- L-GULURONIC ACID

This is a continuation of application U.S. Ser. No. 07/619,313, filed Nov. 27, 1990, now abandoned, which is continuation-in-part of application U.S. Ser. No. 07/446,462, filed Dec. 5, 1989, now abandoned.

BACKGROUND OF THE INVENTION

1. Field of the Invention

This invention relates to the fields of polymer chemistry, immunology and transplantation, and more particularly to the field of materials for use in conjunction with transplantation and implantation of foreign cells and biological materials.

2. Art Background

Evidence exists that transplantation of insulin-producing cells (islets) can cure the diabetic animal of the need for insulin therapy. The major obstacle preventing clinical success in islet transplantation as a therapy for diabetes to date has been immunogenicity of the cell and rejection of the transplanted graft. Survival of islet allografts and or xenografts has been achieved by various methods of immunosuppression and/or related immunological techniques. However, such techniques have had only limited success in that the transplanted islet cells survive only a short while before rejection occurs. In addition, the extended use of immunosuppressive agents often results in severe complications, such as, renal damage and even cancer in the transplant recipient.

One solution to this problem of graft rejection is the introduction of a physical, semi-permeable barrier between the transplanted islets and the host's immune system by the method of microencapsulation. Microencapsulation is a process in which small, discrete materials, viable biological tissue or cells, liquid droplets, or gases are completely enveloped by an intact membrane which is preferably compatible with the biological system in which it is placed. The function of the microcapsule membrane is to protect the material within from immunological recognition by the host and to control the flow of materials inside and outside the microcapsule across the membrane.

A large body of literature on microencapsulation has been produced including Darquy, S. and Reach, G. *Diabetologia,* (1985) 28:776–780; Lim, F. and Sun, A. *Science,* (1980) 210:908–910; Lim, F. and Moss, R. *Journal of Pharmaceutical Sciences,* (April, 1981) 351–354; O'Shea, et al. *Biochemica et Biophysica Acta.* 804 (1984) 133–136; Leung, et al. *Artificial Organs,* (1983) 7(2):208–212; Araki, et al. *Diabetes,* Vol. 34, September 1985, 850–854; and U.S. Pat. Nos. 4,690,682; 4,409,331; 4,391,909; among others.

In addition to islet cells, other materials such as tissue, charcoal, microbial cells, yeasts, chloroplasts, plant protoplasts, mitochondria and enzymes have been immobilized and entrapped using microencapsulation techniques.

Attempts have been made to transplant such encapsulated material into a patient to perform the specific function of that material inside the recipient patient. For example, activated charcoal could be used to detoxify blood, while pancreatic tissue could supplement the patient's supply of insulin. See, e.g., Lim and Sun (1980) Science 210, 908; O'Shea, et al. (1984) Biochim. Biophys. Acta 804, 133.

While such attempts have been partially successful, the patient's body often reacts in ways that impair the activity of the microcapsules by fibroblast overgrowth of this substance by the body. A potential mechanism for the induction of fibroblasts is the activation of macrophages, and the resultant stimulation of cytokines by the capsule substance. Cytokines are molecules secreted by the body in response to a new set of antigens, and are often toxic to the encapsulated cells. Some cytokines in turn stimulate the immune system of the patient. Thus, immune response can still be a limiting factor in the effective life of the encapsulated material.

In addition, fibroblast cells tend to overgrow the microcapsules, also apparently in response to the newly released cytokines. Dinerallo, in LYMPHOKINES AND THE IMMUNE RESPONSE (Cohen, ed. 1990) CRC Press, p. 156; Piela and Korn, in LYMPHOKINES AND THE IMMUNE RESPONSE (Cohen, ed. 1990) CRC Press, pp. 255–273. This growth of fibroblasts causes the microcapsules to lose their porosity. As a result, the cellular material inside the microcapsules cannot receive nutrients and the product of the cellular material cannot permeate the microcapsule wall. This can cause the encapsulated living material to die, and can impair the effectiveness of the microcapsules as a delivery system.

Among the materials used for encapsulation are calcium alginate gels. Lim and Sun, in 1980, successfully microencapsulated islets using alginate gel, poly-L-lysine and polyethylenimine. The encapsulated islets were injected intraperitoneally into diabetic rats. The animals' blood glucose levels dropped to normal for two to three weeks, suggesting that the encapsulation process had protected the islets from invasion by the recipients' immune system. However, these studies showed that the microcapsules were eventually rejected as a result of fibrosis, or fibroblast formation around the microcapsule, which eventually restricts the flow of nutrients to the cells contained in the microcapsule and the outflow of material from the microcapsules created by the islet cells disposed therein.

Alginate, the principal material of the microcapsules, is a heterogeneous group of linear binary copolymers of 1–4 linked β-D-mannuronic acid (M) and its C-5 epimer α-L-guluronic acid (G). The monomers are arranged in a block-wise pattern along the polymeric chain where homopolymeric regions (M blocks and G blocks) are interspaced with sequences containing both monomers (MG blocks). The proportion and sequential arrangement of the uronic acids in alginate depend upon the species of algae and the kind of algal tissue from which the material is prepared. Various properties of different types of alginates are based upon the guluronic acid makeup of the particular alginate. For example, viscosity depends mainly upon the molecular size, whereas the affinity for divalent ions essential for the gel-forming properties are related to the guluronic acid content. Specifically, two consecutive di-axially linked G residues provide binding sites for calcium ions and long sequences of such sites form cross-links with similar sequences in other alginate molecules, giving rise to gel networks.

Commercial alginates are produced mainly from *Laminaria hyperborea, Macrocystis pyrifera, Laminaria digitata, Ascophyllum nodosum, Laminaria japonica, Eclonia maxima, Lesonia negrescens* and *Saragassum sp.*

Additionally, alginates may be obtained from certain bacteria. *Azotobacter vinelandii* produces O-acetylated alginate with a content of L-guluronic acid ranging from 15 to 90%. *Pseudomonas aeruginose* under certain growth conditions produces poly-mannuronic acid and such bacteria as well as certain other alginate producing Pseudomonades are not able to produce polymers containing G-blocks.

Also, alginates having high or low contents of G or M residues may be obtained from specific portions of algal tissue. For example, alginate having a high content of guluronic acid may be obtained from the outer cortex of old stipes of *L. hyperborea*. Alginate having a high content of guluronic acid can also be prepared by chemical fractionation or by enzymatic modification using mannuronan C-5 epimerase. This enzyme is able to introduce G-blocks into an existing alginate polymer, producing polymers with high G-block content.

It is believed that alginate itself is one of the materials of the microcapsules which causes fibrosis, such that attempted implantation or transplantation of alginate encapsulated material is viable only for a short term.

A measure of the potential to cause fibrosis can be obtained from the ability of certain substances to induce cytokine production, including tumor necrosis factor-$\alpha$ (TNF-$\alpha$), interleukin-1 (IL-1) and interleukin-6 (IL-6). These cytokines play an important role in immune responses and in inflammatory reactions. These macrophage-derived mediators are known to regulate fibroblast proliferation (Libby et al., J. Clin. Invest. (1986) 78:1432; Vilcek et al., J. Exp. Med. (1986) 163:632). A possible mechanism for the fibrotic reaction to implanted microcapsules is the activation of macrophages, either by a contaminant within commercial alginate (e.g., polyphenols or lipopolysaccharides (LPS)), or by alginate monomers directly, with subsequent release of cytokines responsible for fibroblast migration and proliferation. LPS are known to stimulate the immune response. Additionally, polysaccharides other than LPS have been reported to have an immunostimulating effect, including antitumor activity and stimulation of monocyte functions. However, little is known about the effects of polysaccharides on cytokine production from monocytes.

SUMMARY OF THE INVENTION

The present invention provides a successful approach to microencapsulation and implantation which has not heretofore been discovered.

It is one object of the present invention to provide a material which may be implanted or transplanted in vivo which is non-immunogenic and non-fibroblast inducing.

It is yet another object of the present invention to provide a microencapsulation system utilizing purified alginate having a high guluronic acid content.

It is another object of the invention to provide a microencapsulation system which does not include poly-L-lysine in its outer coating and which eliminates the growth of fibroblasts around the microcapsules.

It is yet another object of the present invention to provide a microcapsule which does not induce tumor necrosis factor (TNF) or interleukin release and thereby prevents fibroblast formation therearound.

It is another object of the present invention to provide a microencapsulation system which is substantially nontoxic to the cells by minimizing the amount of poly-phenol in the alginate.

It is an object of the present invention to provide a composition and means for reducing production of cytokines such as TNF, IL-1 and IL-6 production in vivo.

It is another object of this invention to provide a composition and means for preventing or treating sepsis caused by TNF, IL-1 and/or IL-6 production.

The present invention provides a material comprised of alginate, and particularly, alginate comprising primarily guluronic acid, with minimal amounts of mannuronic acid, the material being useful in vivo for implantation and transplantation in mammalian bodies. The material may take many forms, such as sheets, organ capsulation and the like, but is preferably used for microencapsulation of living cells and tissue which are foreign to the host in which they are implanted. The present invention also protects islet cells or other transplanted tissue from immunological cell rejection. The present invention also provides a microencapsulation system which limits fibroblast overgrowth.

The present invention also acts to depress production in vivo of cytokines such as TNF, IL-1 and IL-6. As such, it is useful as a pharmaceutical to inhibit the production of these cytokines for such purposes as the treatment of sepsis, immune rejection, and inflammatory response.

Specifically, the present invention relates to encapsulation of cells or other biological material with an outer coating of alginate which is completely or substantially comprised of guluronic acid and is completely or substantially free of mannuronic acid. Additionally, the same alginate can be used in various forms to inhibit cytokine production.

DETAILED DESCRIPTION OF THE INVENTION

The present invention comprises material which can be implanted or transplanted in vivo into mammals without inducing any substantial immunogenic reaction or fibroblast formation. One important use for this material is for encapsulation of biological materials, such as in microcapsules. The present invention is also a process for microencapsulating biological cells and other materials for use in implantation or transplantation as a drug or biological material delivery system. As used herein, the term biological materials includes prokaryotic and eukaryotic cells which are either naturally occurring or genetically engineered, drugs or pharmaceuticals, enzymes, parts of cells such as mitochondria and protoplasts or any other naturally occurring or synthesized material which may be implanted.

The material used in the present invention is alginate comprised substantially of $\alpha$-L-guluronic acid (G) which may be referred to herein as guluronic acid. Small amounts of mannuronic acid ($\beta$-D-mannuronic acid) (M) are also present. There are at least 65% G residues or more, and preferably about 85% G residues and 15% or less M residues. Alginate so comprised elicits a very low response from monocytes in the production of tumor necrosis factor (TNF) and of IL-1 and IL-6, which, as a result, does not elicit fibrosis.

This high-G alginate is used in the formation of microcapsules for the transplantation or implantation of foreign material into a mammal. The high-G alginate is used in place of at least one layer of polyanionic polymer, such as low-G alginate, in the microcapsule membrane. The high-G alginate can be used as the inner or first layer surrounding the encapsulated material. In some microcapsules this may be the only layer surrounding the encapsulated material. Additionally a second layer of polyanionic polymer can be used, either immediately surrounding the gelled first layer, or surrounding a second layer made of a polycationic polymer. Alternatively, the polyanionic polymer layer can be used as the second layer surrounding a first layer made of either a polycationic polymer or a basement membrane. Preferably, the outermost layer of polyanionic polymer is high-G alginate. Any other layer of polyanionic polymer can also be composed of high-G alginate. Procedures for making microcapsules are well known in the art and examples are described in, for example, Lim and Sun, "Microencapsulated islets as bioartificial endocrine pancreas" Science: 1980; 21:908; O'Shea et al, "Prolonged survival of transplanted islets of Langerhans encapsulated in a biocompatible membrane". *Biochim Biophys Acta* 1984: 804: 133; Goosen et al, "Optimization of microencapsulation parameters: Semipermeable microcapsules as a bioartificial pancreas"; *Biotechnol Bioeng* 1985; 27: 146; Sun et al "Transplantation of microencapsulated isles of Langerhans as a insulin deliver system" *Topics in Pharmaceutical Sciences* 1985; 93; Tze et al, "Biocompatibility and immunological studies of microencapsulation with cross-linked alginate capsules;" *Transplantation* 1982; 33; 563; Sun and Lim (1980) Science, 210:908–910, Tsang et al. U.S. Pat. No. 4,663,286, and Rha et al. U.S. Pat. No. 4,744,933 (May 17, 1988), which are incorporated herein by reference.

Material to be implanted or transplanted is first coated with a negatively charged material such as alginate to form a gel coating therearound, as described above. Alternatively, the cellular material is coated with a tissue basement membrane such as Matrigel (Collaborative Research, Inc., Bedford, Mass.). The solubilized tissue basement membrane contains proteoglycans, collagen, and laminin and/or intactin. By use of the Matrigel, the proteoglycan forms a matrix which permits transfer of selected materials inside and out of the cells. Further, the use of the tissue basement membrane eliminates the need for a gelling and then reliquification of the gel material surrounding the cell. Additionally, it is believed that the tissue basement membrane provides both structural elements supporting the cells and also mediates various significant cellular events and cellular functions including proliferation and differentiation. Thus, by incorporation of the structural elements of the extracellular matrix of the tissue basement membrane or an equivalent thereof into a microencapsulated bioenvironment, the viability and functionality of the immuno-isolated islet cells is enhanced. This environment not only enhances islet recovery but the microencapsulation process also contributes to the long term viability and function of the islet cells. In the preferred embodiment, the molecular weight of the proteoglycans used as the tissue basement membrane have a molecular weight of 200,000 to 300,000 Daltons.

Following coating of the transplantable material with the tissue basement membrane matrix or an equivalent thereof, the transplantable material is next coated with a positively charged material such as poly-L-lysine. The use of poly-L-lysine as a coating material is well-known in the art and is described in various references referred to above. It has been found, however, that the use of poly-L-lysine having a molecular weight of less than 20,000 is particularly advantageous in that it minimizes the induction of fibroblast formation. Alternatively, a positively charged polysaccharide such as chitosan may be used as the second layer of the coating.

As a third and outer coating layer, the positively charged second layer is coated with a layer of alginate of the present invention comprising high G content, greater than 65% and preferably greater than 85% G residues, as described above. However, it should be noted that any minimization of mannuronic acid residues, with the equivalent increase in G residues in the alginate, is contemplated by the present invention and will enhance the decrease of fibrosis.

For in vivo applications of the present invention, the composition comprising alginate having a high G content may be used in the form of organ capsulation, sheets of alginate for implantation, hollow fibers, microcapsules and membranes formed of the subject composition.

In accordance with these findings, the present invention comprises the use of Poly G alginate as a coating material for any biological materials which may be implanted or transplanted. The material to be implanted or transplanted can include living tissue, living cells, activated charcoal, or any other material of the appropriate size which is useful when transplanted within immunoisolation systems. Material to be transplanted is preferably chosen for its ability to function in vivo when transplanted into a recipient body. Living cells can include, but are not limited to, islets of Langerhans cells which can produce insulin, hepatic cells or liver tissue, and red blood cells. In particular, cells such as islet cells from the Islets of Langerhans may be purified in accordance with co-pending application Serial No. 232,328 or by other methods known in the art.

Experiments were run to test the efficacy of high-G alginate in microcapsules. High-G alginate was used to make microcapsules that were tested for cellular response. These responses were compared to responses elicited by alginates with a variety of compositions: high-M alginate, alginate with continuous blocks predominantly composed of M (M blocks), and alginate with continuous blocks predominantly composed of G (G blocks). Induction of various cytokines were tested, including TNF, IL-1 and IL-6, as a means of monitoring the immune response to the various alginates.

Microcapsules with at least one outer layer composed of high-G alginate were found to elicit the lowest amounts of the various cytokines. See FIGS. 1–6. As a result, such microcapsules would be the most effective for implantation or transplantation of material into a mammalian body, because they would minimize the immune response by the body to the microcapsules.

For use in this invention, alginate can be prepared according to methods well known in the art. For example, alginate can be commercialy obtained from numerous outlets including Sigma (St. Louis, Mo.) and Protan A/S (Drammen, Norway). Poly G alginate may be obtained from Protan (Norway or Seattle), or may be obtained by isolation of the material from natural sources or by chemical conversion by methods reported in the literature. Some alginate is relatively high in M residues and must be converted to low M for use in this invention. An example of a procedure which can be used for reducing the level of M in alginate follows.

Figure 2:
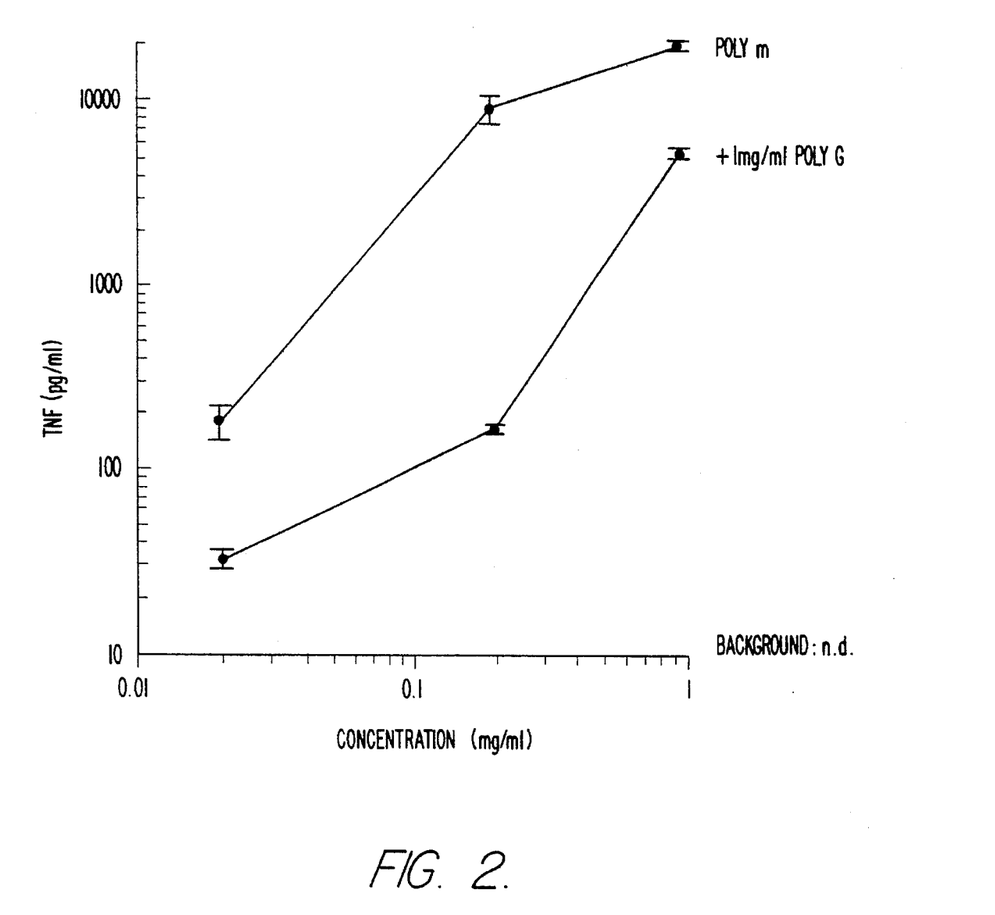
FIG. 2 is a graph showing the dampening effect of induction of TNF by Poly G when combined with Poly M.
Figure 4:
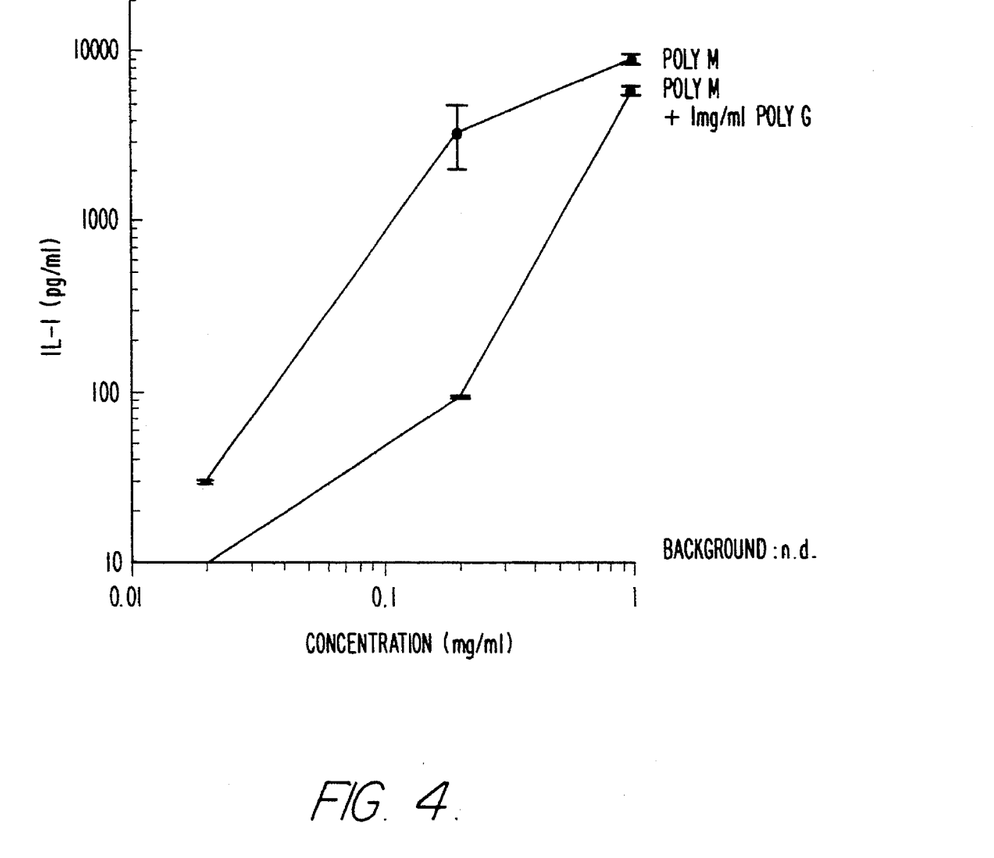
FIG. 4 is a graph showing the dampening effect of induction of IL-1 by Poly G when combined with Poly M.
Figure 6:
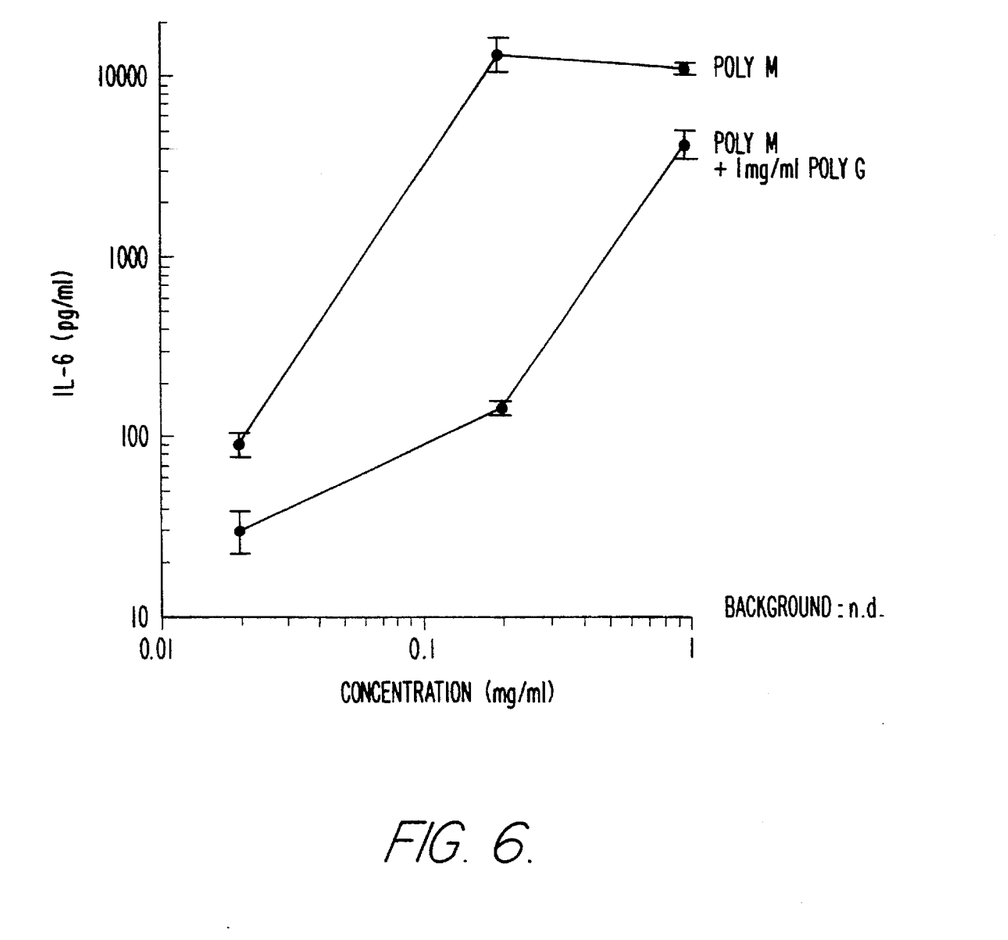
FIG. 6 is a graph showing the dampening effect of induction of IL-6 by Poly G when combined with Poly M.

Another use for the composition of this invention is to inhibit in vivo production of cytokines such as TNF, IL-1 and IL-6. As FIGS. 2, 4, and 6 show, the high-G alginate depresses production of both of these cytokines. These cytokines play a role in a number of disease states, including but not limited to inflammatory response, transplant rejection, and sepsis. Therefore, this high-G alginate composition can be administered to treat such disease states. The concentration of high-G alginate useful for such treatment is shown in FIGS. 2, 4 and 6, Table 1, and described in Examples 5 and 6, below.

EXAMPLE 1

Alginate Preparation

Commercial alginate from the algae *Laminaria hyperborea* (LF 10/60, batch nr. BL 5417368) containing 64% guluronic acid residues was obtained from Protan A/S, Drammen, Norway. LPS contamination in the alginate was removed by the method described by Karplus et al. ("A new method for reduction of endotoxin contamination from protein solutions"; *J. Immunol. Methods,* (1987) 105: 211) using a combination of Polymyxin-B-sepharose 4B (PB-seph 4B) (Pharmacia, Uppsala, Sweden) affinity binding and endotoxin-protein dissociation with the dialyzable surfactant octyl-β-D-glucopyranoside (OBDG) Sigma, St. Louis, Mo., U.S.A.).

Briefly, 1% (w/v) OBDG was added to 1% (w/v) LF 10/60 solution (dissolved in elution buffer consisting of $NaHCO_3$ pH 8.5), and mixed for 30 min. at room temperature. Equal volumes of the PB-Seph 4B-gel and OBDG/alginate solution were mixed and transferred to a dialysis bag (MW 12–14000). The bag was then placed in a container with phosphate buffered saline (PBS) and dialyzed for 48 hours at room temperature. Subsequently, the PB-Seph 4B-gel was removed by centrifugation at 2750 r.p.m., for 10 min. at 4° C. 0.2% NaCl (w/v) was added to the alginate solution and the alginate was precipitated with 96% ethanol. The alginate was then washed twice with 96% ethanol and finally once with 96% ethanol and once with diethylether before it was dried. This alginate is referred to herein as poly-G alginate or G-block alginate.

For studies comparing the effects of high M and high G alginate, as well as alginates having M blocks and G blocks, on cellular responses, various types of alginate were obtained as follows:

M-block alginate (95% M and degree of polymerization $(DP_n)=35$) was obtained from an alginate enriched mannuronic acid isolated from the intracellular substance of *Ascophyllum nodosum* (*A.nodosum*) fruiting bodies as described by Haug et al. ("Correlation between chemical structure and physical properties of alginates" *Acta Chem Scand* 1967:21:768).

Alginate fragments containing more than 85% of G units and $DP_n=40$ (G-blocks) were prepared from *Laminaria digitata*. Alginate fragments with predominantly an alternating structure, MG-blocks (63% M and $DP_n=25$) were isolated from *A. nodosum* by the method described by Haug et al. ("Studies on the sekvens of uronic acid residues in alginic acid" 1967:21:691).

An alginate sample with a lower content of guluronic acid residues (46%) was isolated from tissues of *A. nodosum* as described by Haug et al.

The monomer composition and sequential arrangement as well as the DPn were analyzed by $^1$H-n.m.r. spectroscopy on a Bruker 400 WM spectrometer as described previously by Grasdalen et al. ("A p.m.r. studie of composition and sequence of uronate residues in alginate"; Carbohydr Res 1979; 68:23).

Endotoxin content in the purified and unpurified alginates was quantified by the LAL-assay (Coatest Endotoxin from Kabi Vitrum, Stockholm, Sweden).

EXAMPLE 2

Monocyte Cultivation

Monocytes were isolated from human A+ blood buffy coat (The Bloodbank, University of Trondheim, Norway) as described by Boyum ("Separation of monocytes and lymfocytes." Scan J lmmunol 1976; 5:9). Monocytes in 24 well culture plates (Costar, Cambridge, Mass., U.S.A.) were cultured in complete medium consisting of RPMI 1640 (Gibco, Paisley, U.K.) with 1% glutamine, 40 mg/ml garamycin and 25% A− serum. (The Bloodbank, University of Trondheim).

The alginate, the M-blocks, the G-blocks and the MG blocks were dissolved in PBS and sterile filtered through 0.2 μm filter (Nuclepore, Pleasanton, Calif., U.S.A.). Commercial unfiltered alginate was sterilized by autoclaving. The polysaccharide solutions were diluted in complete medium and added to the monocytes for 16-24 hours before the supernatants were harvested. *E. coli* (strain 026:06) derived LPS (Sigma), or b/1-3 D polyglucose (obtained from Professor R. Seljelid, University of Tromse, Norway) were added to some monocyte cultures.

Alginate gels were made in 24-well culture plates (Costar) by adding 0.5 ml 10 mg/ml sterile filtered alginate solution in the wells. Then 1 ml of 0.1 M $CaCl_2$ was added for 10 min. before the supernatant over the gel was removed. The gels were then washed twice with 1.5 ml saline, and finally twice with complete medium. Human monocytes at a concentration of $0.5\times10^6$ cells/well were added to the alginate gels, and the plate was incubated for 16–24 hours before the supernatants were harvested.

EXAMPLE 3

Assay for Detection of TNF-α in Supernatants From Monocytes

Amount of TNF-α was determined by its cytotoxic effect on the fibrosarcoma cell line WEHI 164 clone 13, as described in Espevik et al ("A highly sensitive cell line, WEHI 163 clone 13, for measuring cytotoxic factor/tumor necrosis factor from human monocytes." *Immunol Methods* 1986; 95:99.) Dilutions of recombinant TNF-α (r-TNF-α, Genentech, Inc. South San Francisco) were included as a standard. The TNF-α specificity of the assay was verified by a monoclonal antibody against rTNF-α which completely neutralized the recorded activity (data not shown).

EXAMPLE 4

Assay for Detection of IL-1 in Supernatants from Monocytes:

Amount of IL-1 was determined by a two stage assay. The first stage involves the mouse thymocyte EL-4 NOB-I cell line which produces high concentrations of IL-2 (interleukin-2) in response to human IL-1, as described by Gaering et al. Dilutions of r-IL-1 (Glaxo, Geneva, Switzerland) were included as standard. After incubation in $CO_2$ for 24 hours, 100 ml of each of the supernatants were transferred into replicate 96-well microplates. The second stage in this assay involves the IL-2 dependent mouse T cell line HT-2 as described by Mosmann, T. ("Rapid colorimetric assay for cellular growth and survival: Application to proliferation and cytotoxicity assays." J. Immunol 1987; 139:4116). One hundred ml of HT-2 suspension ($1.2\times10^5$ cells/ml were added to each well and incubated for an additional 24 hours. The IL-1 activity was completely neutralized by two polyclonal antibodies against rIL-1b. Results are presented as pg/ml +/− S.E. of triplicated determinations.

EXAMPLE 5

Viability Using MTT-assay (3-(4,5-dimethylthiazol-2-yl)-2,5-diphenyltetrazolium bromide)

Viability in the assays for TNF-α, IL-1 and IL-6 was measured in a colorimetric assay for growth and survival by using a tetrazolium salt as described by Mosmann, supra.

Figure 1:
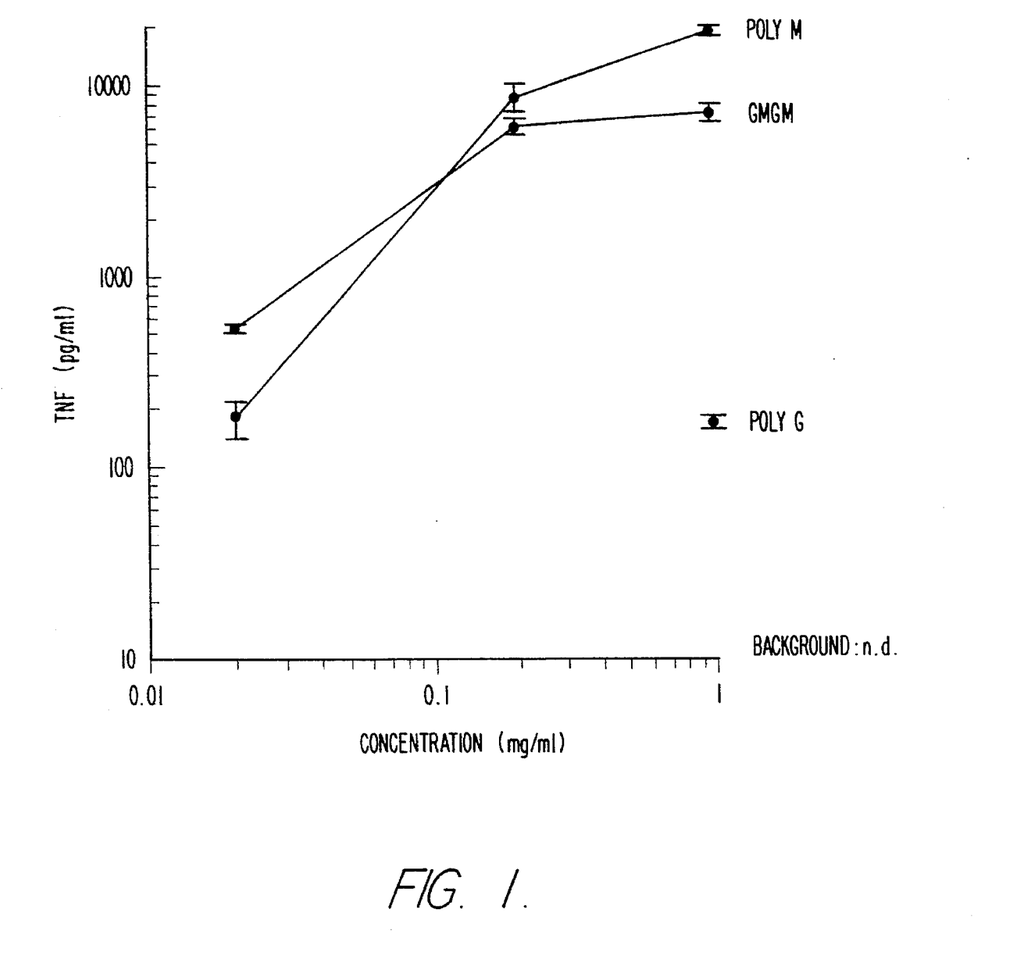
FIG. 1 is a graph showing the induction of TNF by Poly M, heterologous GMGM polymeric and Poly G alginates.
Figure 3:
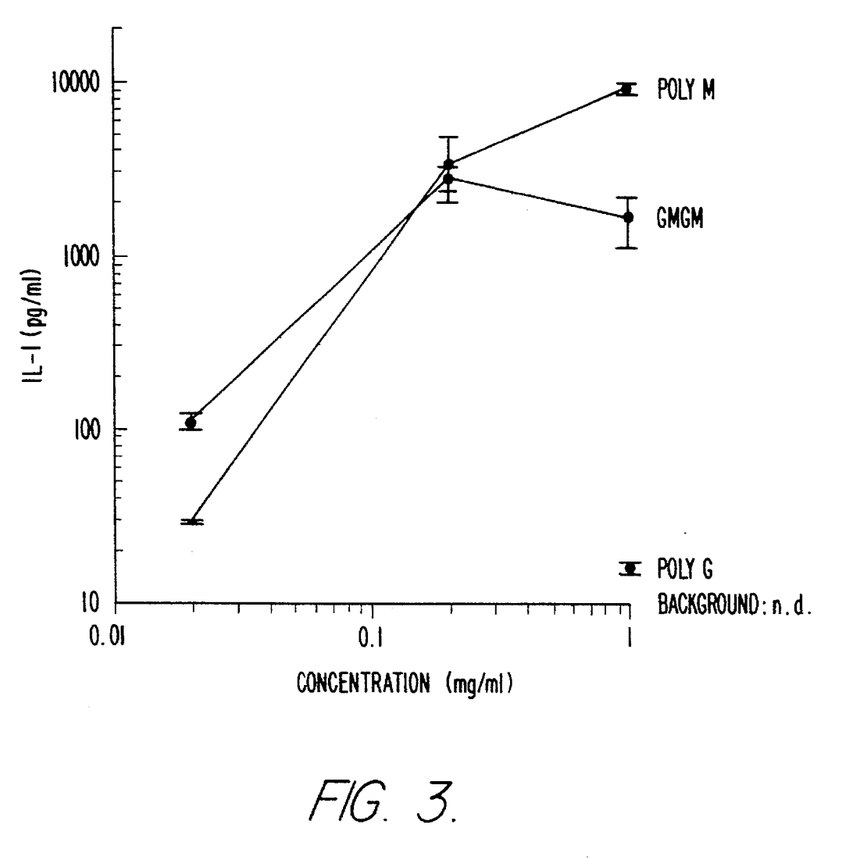
FIG. 3 is a graph showing the induction of IL-1 by Poly M, heterologous GMGM polymeric and Poly G alginates.
Figure 5:
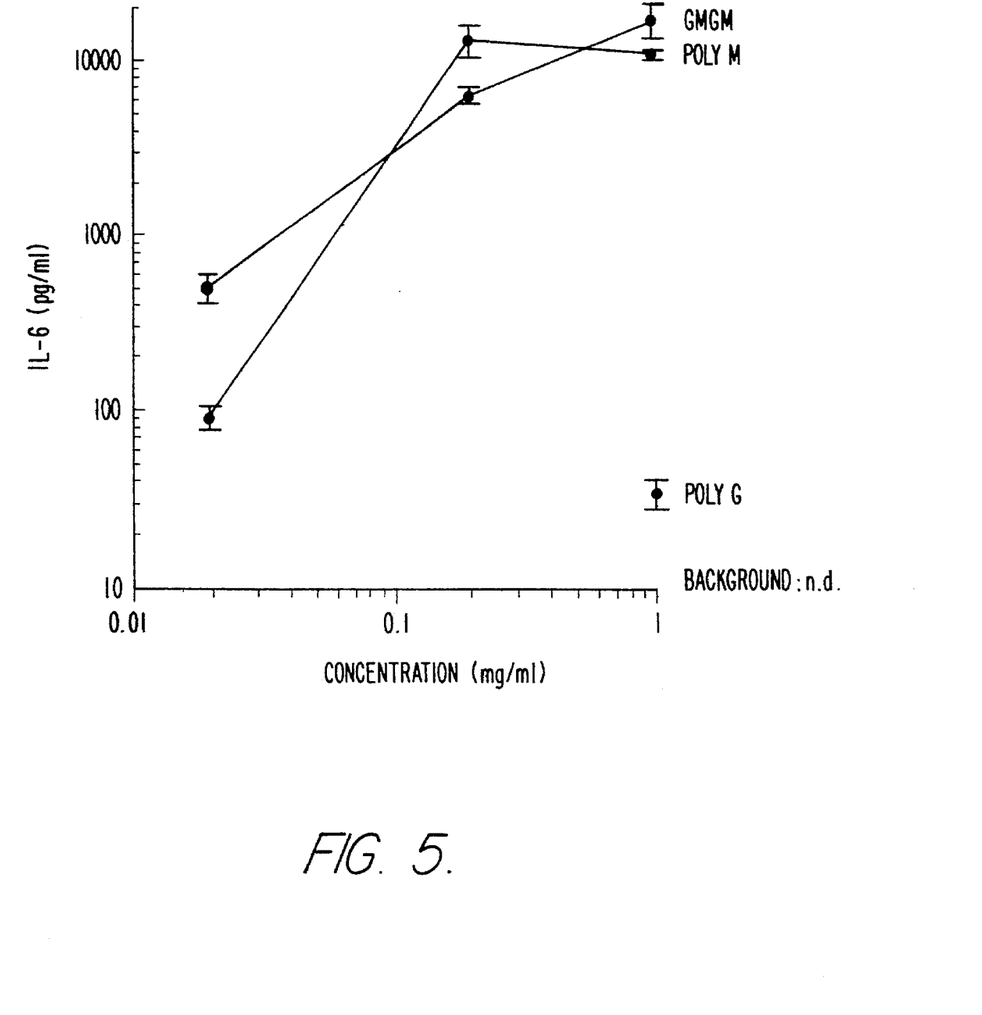
FIG. 5 is a graph showing the induction of IL-6 by Poly M, heterologous GMGM polymeric and Poly G alginates.

As shown in FIG. 1, three separate alginate compositions were tested for their ability to induce monocytes to release TNF. The alginate compositions included Poly G alginate, heterologous GMGM alginate comprising linear binary copolymers of 1–4 linked β-D-mannuronic acid (M) and its C-5 epimer α-L-guluronic acid (G), and Poly M (β-D-mannuronic acid) alginate. The foregoing three types of alginate material are referenced in FIGS. 1 through 6 as Poly G, GMGM and Poly M. The alginates were dissolved in tissue culture medium in varying concentrations set forth in FIG. 1, 3 and 5 in which equal concentrations of monocytes were placed. FIG. 1 shows that Poly M and GMGM alginate induced substantial TNF production by the monocytes on the order of 7000 to 10,000 picograms of TNF per milliliter, whereas Poly G alginate induced TNF production two orders of magnitude less, or at approximately 200 pg/ml of TNF. TNF is known as an inducer of fibroblast growth. FIG. 3 shows the equivalent results with respect to IL-1 production by the monocytes. FIG. 5 shows the equivalent results with respect to IL-6 production.

As shown in FIG. 2, Poly G apparently inhibits the production of TNF by monocytes. FIG. 2 shows the results of an experiment in which Poly M and Poly M plus 1 mg/ml of Poly G was added to a culture of monocytes and the TNF production was measured. As can be seen from the graph, the Poly M plus Poly G sample induced substantially lower TNF production than Poly M alone. Thus it appears that Poly G not only has very limited TNF induction capability, it also inhibits Poly M alginate's ability to induce TNF production of monocytes, and accordingly, would inhibit Poly M alginate induction of fibrosis. FIG. 4 shows the equivalent results with respect to IL-I production by the monocytes. FIG. 6 shows the equivalent results with respect to IL-6 production.

EXAMPLE 6

Growth of Monocytes on Alginate Gel

Table 1 shows the results of an experiment which demonstrates cytokine release from monocytes cultured on alginate gels. Monocytes on tissue culture plates were detached by a rubber policeman, washed once in Hanks Balanced Salt Solution, and added to culture wells with alginate gel, or culture wells with LPS or growth media. Alginate gels were made as described above. Supernatants were harvested after 16–24 hours and assayed for TNF, IL-6 and IL-1. As can be seen from the table, the monocytes cultured on LF 10/60, which has a 64% G residue content, induced substantially less production of each of TNF, IL-1 and IL-6 compared with A. nodosum alginate gel, which has a G residue content of 46%. LPS also showed a great capacity to induce cytokine production.

TABLE 1

CYTOKINE RELEASE FROM MONOCYTES CULTURED ON ALGINATE GELS

| Treatment | TNF-α(pg/ml) | IL-6 (pg/ml) | IL-1 (pg/ml) |
|---|---|---|---|
| LF 10/60 alginate gel | 7000 + 1 − 1100 | 10900 + 1 − 1600 | 6400 + 1 − 100 |
| A. nodosum alginate gel | 15600 + 1 − 5300 | 15200 + 1 − 2000 | 16300 + 1 − 800 |
| 1 µg/ml LPS | 12400 + 1 − 2600 | 22200 + 1 − 5100 | 9600 + 1 − 900 |
| Growth Medium | 50 + 1 − 10 | 70+ 1 − 20 | 90+ 1 − 10 |

EXAMPLE 7

Microencapsulation of Islets of Langerhans.

Cultured rat islets of Langerhans ($2\times10^3$ islets in 0.2 ml medium) were suspended uniformly in 2 ml of a 1.5% (w/w) sodium alginate solution (viscosity 51 cps) in physiological saline. Spherical droplets containing islets were produced by syringe pump/air jet extrusion through a 22-gauge needle and collected in 1.5% (w/w) calcium chloride solution. The supernatant was decanted and the gelled spherical alginate droplets, containing islets, were washed with dilute CHES (2-cyclohexylamino-ethane sulfonic acid) solution and 1.1% calcium chloride solution.

After aspirating off the supernatant, the gelled droplets were incubated for 6 minutes in 0.05% (w/w) polylysine having a molecular weight of 17,000.

The supernatant was decanted and the polylysine capsules were washed with dilute CHES, 1.1% calcium chloride solution and physiological saline. The washed polylysine capsules were incubated for 4 minutes in 30 ml of 0.03% sodium alginate to permit the formation of an outer alginate membrane on the initial polylysine membrane, by ionic interaction between the negatively charged alginate and the positively charged polylysine. The alginate used in the outer and inner coating is poly G alginate produced as described above.

The resulting microcapsules were washed with saline, 0.05M citrate buffer for 6 minutes to reliquify the inner calcium alginate, and washed again with saline. The microcapsules were found to be perfectly spherical and each to contain from 1 to 2 viable islets. The microcapsules had diameters of 700±50 µm and wall thicknesses of about 5 µm. The microcapsules were suspended in nutrient medium at 37° C.

It will be obvious to a person of ordinary skill in the art that the present invention is not limited in its application to specific biological materials to be encapsulated, such as the islet cells described in detail above, or by the specifically described other inner layers of microcapsule discussed herein. It will also be appreciated that the subject invention is not limited to only three layer microcapsules, but that two layer capsules may also be employed using the high G content alginate of the present invention, and if desired, the low molecular weight poly-L-lysine (below 20,000 daltons). The only limitations of the present invention are set forth in the claims appended hereto and any equivalents thereof.

We claim:

1. A transplantation or implantation composition which provokes a reduced immune response comprising material encapsulated within a physical semi-permeable barrier comprised of a gel prepared by gelling alginate containing at least 85% α-L-guluronic acid with calcium ions, wherein said material is comprised of viable mammalian cells.

2. A transplantation or implantation composition which provokes a reduced immune response comprising material encapsulated within a physical semi-permeable barrier comprised of a gel prepared by gelling alginate containing at least 85% α-L-guluronic acid with calcium ions, wherein said material is comprised of genetically modified cells.

* * * * *